United States Patent
Prakash et al.

(10) Patent No.: US 9,990,471 B2
(45) Date of Patent: Jun. 5, 2018

(54) SYSTEMS AND METHODS FOR FACILITATING INTEGRATED BEHAVIORAL SUPPORT

(71) Applicants: Adityo Prakash, Fremont, CA (US); Eniko Fodor, Fremont, CA (US)

(72) Inventors: Adityo Prakash, Fremont, CA (US); Eniko Fodor, Fremont, CA (US)

(*) Notice: Subject to any disclaimer, the term of this patent is extended or adjusted under 35 U.S.C. 154(b) by 0 days. days.

(21) Appl. No.: 14/217,165

(22) Filed: Mar. 17, 2014

(65) Prior Publication Data

US 2014/0278513 A1    Sep. 18, 2014

Related U.S. Application Data

(60) Provisional application No. 61/801,454, filed on Mar. 15, 2013.

(51) Int. Cl.
*G06Q 50/22* (2018.01)
*G06F 19/00* (2018.01)
(Continued)

(52) U.S. Cl.
CPC ....... *G06F 19/345* (2013.01); *G06Q 30/0601* (2013.01); *G16H 50/20* (2018.01);
(Continued)

(58) Field of Classification Search
CPC .............. G06F 19/345; G06F 19/3456; G06F 19/3481; G06F 17/30; G06F 19/30; G06F 19/32; G06F 19/321; G06F 19/324; G06F 19/325; G06F 19/326; G06F 19/328; G06F 19/34; G06F 19/3418; G06F 19/3462; G06F 19/3468; G06F 19/3475; G06F 19/36; G06Q 30/0601; G06Q 50/22; G06Q 50/24; A61N 1/08; G16H 10/00; G16H 10/20; G16H 10/40; G16H 10/60; G16H 10/65;
(Continued)

(56) References Cited

U.S. PATENT DOCUMENTS

| | | | |
|---|---|---|---|
| 2005/0075931 A1 | 4/2005 | Pearson | |
| 2005/0178828 A1 | 8/2005 | Agostino et al. | |
| 2006/0218011 A1* | 9/2006 | Walker | A61J 7/0481 705/3 |
| 2006/0224450 A1* | 10/2006 | Moon | G06Q 30/02 705/14.36 |

(Continued)

*Primary Examiner* — Tran N Nguyen
(74) *Attorney, Agent, or Firm* — Klintworth & Rozenblat IP LLP

(57) ABSTRACT

The present invention includes various embodiments of a BSA system that facilitates the collection of relevant health-related data on a continuous basis, integrates such data with pertinent personal and aggregate information, enables users to purchase (directly and indirectly) health-related goods and services, and provides credit, discounts and other economic benefits in connection with such purchases that are determined dynamically based upon the nature and extent of users' interaction with the system. The BSA system facilitates a dynamic feedback process by continually monitoring user interaction and medical and financial behavior, which results in dynamic adjustments to their credit levels and offers of discounts and other promotions, which in turn incentivizes users to continue participating in the process (thereby modifying their system interactions and behavior, and thus perpetuating this feedback loop). As a result, users are incentivized to actively participate in the process and thereby enhance their wellness while reducing healthcare costs.

12 Claims, 8 Drawing Sheets

(51) Int. Cl.
*G06Q 30/06* (2012.01)
*G06Q 50/26* (2012.01)

(52) U.S. Cl.
CPC ...... *G06F 19/3456* (2013.01); *G06F 19/3481* (2013.01); *G16H 50/70* (2018.01)

(58) Field of Classification Search
CPC ........ G16H 15/00; G16H 20/00; G16H 20/10;
G16H 20/13; G16H 20/17; G16H 20/30;
G16H 20/40; G16H 20/60; G16H 20/70;
G16H 20/90; G16H 30/00; G16H 30/20;
G16H 30/40; G16H 40/00; G16H 40/20;
G16H 40/40; G16H 40/60; G16H 40/63;
G16H 40/67; G16H 50/00; G16H 50/20;
G16H 50/30; G16H 50/50; G16H 50/70;
G16H 50/80; G16H 70/00; G16H 70/20;
G16H 70/40; G16H 70/60; G16H 80/00
See application file for complete search history.

(56) References Cited

U.S. PATENT DOCUMENTS

| | | |
|---|---|---|
| 2007/0100595 A1 | 5/2007 | Earles et al. |
| 2007/0150355 A1* | 6/2007 | Meggs ............... G06Q 30/02 705/14.17 |
| 2008/0001735 A1* | 1/2008 | Tran ................... G06F 19/3418 340/539.22 |
| 2008/0197185 A1* | 8/2008 | Cronin ............... G06F 19/328 235/375 |
| 2008/0255979 A1* | 10/2008 | Slutzky ............. G06F 19/328 705/35 |
| 2008/0281767 A1* | 11/2008 | Garner ............... G06N 3/088 706/25 |
| 2010/0070359 A1 | 3/2010 | Heasley et al. |
| 2012/0244504 A1 | 9/2012 | Wasserman |
| 2012/0265546 A1* | 10/2012 | Hwang ............. G06F 19/3456 705/2 |

* cited by examiner

SYSTEMS AND METHODS FOR FACILITATING INTEGRATED BEHAVIORAL SUPPORT

CROSS REFERENCE TO RELATED APPLICATIONS

This application claims the benefit, pursuant to 35 U.S.C. § 119(e), of U.S. Provisional Patent Application No. 61/801,454, filed Mar. 15, 2013, entitled "Systems and Methods for Facilitating Integrated Access to Health Information," which is hereby incorporated by reference in its entirety.

BACKGROUND

Field of Art

The present invention relates generally to interactive support and modification of user behavior patterns, and more particularly to interactive healthcare and a novel variation of a behavioral support agent that incentivizes individuals to interact with and actively participate in utilizing online resources to enhance their overall wellness.

Description of Related Art

As the Internet evolves, access to information, including health-related information, continues to increase exponentially. Individuals currently have instant online access, from a wide variety of sources, to personal and aggregate information relating to patient histories, test results, physical and mental fitness, nutrition, health supplements, and a vast array of health research, as well as methods and devices for measuring, diagnosing and treating various conditions or simply enhancing overall wellness.

Moreover, the advent of "smart" mobile devices and related technologies has provided individuals with access to such information on a continuous basis, as well as the ability to monitor health-related data (heart rate, blood pressure, etc.) and receive feedback covering virtually any period of time, including events such as a workout or a night's sleep.

However, this vast of array of information and device technology is far from integrated, and can be overwhelming to individuals. How does a layperson even identify relevant symptoms, much less sift through the vast array of available information "on demand" to obtain useful results? And how personalized are those results given the limited amount of data provided by a few search terms? Does a search engine know what medications patients are taking, or whether they recently stopped taking a particular medication, or took another substance or engaged in an activity that, in combination, might explain certain symptoms?

There is clearly a need for a more holistic approach, particularly in light of the state of the technology currently available. In essence, there is a need for a "behavioral support agent" (BSA) that can facilitate the collection of relevant data on a continual basis, integrate such data with pertinent aggregate information, and guide individuals toward behaviors that will enhance their overall wellness.

Various attempts to address one or more aspects of this problem have been implemented or proposed. For example, websites such as WebMD provide users with the ability to search an extensive database of health-related information. In addition to providing a searchable database, other features include a "symptom checker" (which provides potential diagnoses based upon users' answers to questions relating to symptoms) and a "medication tracker" (which enables users to maintain lists of their current medications, and provides information relating to drug interactions, side effects, and FDA warnings). As noted above, however, such "on demand" systems provide limited personalization, as the information they provide is based on keyword searches rather than personal health-related data collected on a continual basis over time.

Other websites and smartphone apps are targeted at specific aspects of healthcare, such as maintaining personal medical records or medication profiles (e.g., HealthVault or MphRx) or monitoring activity and fitness levels, often in connection with user monitoring devices (e.g., FitBit). While some of these approaches may be more engaging than searchable websites, they do not take a holistic approach. Beyond specific activities such as walking, running or taking a pill, they lack comprehensive day-to-day and historical monitoring of users' symptoms, schedules and overall health conditions and the ability to use such data to adapt responses and support provided to the users with a view to improving their health outcomes.

Other systems have adopted a more holistic approach to this problem. For example, U.S. Pat. No. 8,170,609 discloses a personal virtual assistant system that includes a remote station carried by users which has one or more physiological sensors, and a rules engine that provides advice to users based in part upon the sensor data. Other systems have attempted to reduce the need for human intervention in routine aspects of healthcare by programming virtual assistants to aid users in various tasks. For instance, the "Alme" virtual assistant platform from NextIT provides automated aid with navigation of choices for users. It has been recently deployed by Aetna to help members navigate their website better. Ann, Alme's virtual assistant deployed by Aetna, is able to help the insured register on the website, get cost of service estimates, locate in-network providers and compare costs by facilities and physicians. Implementing Ann has enabled Aetna to cut costs by reducing the burden on their call center.

While some of these proposed "solutions" take a more patient-centric and preventive approach to wellness, some key obstacles remain unaddressed, even by existing virtual assistant systems. For example, healthcare is an expensive proposition. Regardless of the quality of the information obtained online, individuals may still find it necessary or desirable from time to time to visit clinics, hospitals, doctors and other specialists, and purchase medications, supplements, health monitoring devices and other health-related goods and services. The cost of such health-related goods and services can be quite significant, despite preventive measures. Additional cost-reduction efforts are still needed to address this problem effectively.

Moreover, as is the case with healthcare generally, the quality of information generated by any of these systems depends greatly upon the degree to which individuals participate in the process and interact with the system. For example, individuals will derive greater benefits if they provide timely and accurate information, follow system suggestions and provide frequent feedback regarding their activities, likes, dislikes and so forth. While users may initially provide profile information and frequently interact with a new system, human behavior is such that, in most cases, their level of interaction quickly tapers off.

While a BSA system could prompt users for relevant information on a timely basis and provide entertaining content in an effort to keep users engaged, additional incentives are needed to maintain sufficient patient participation in the process. Though seemingly unrelated, these problems of high healthcare costs and inadequate patient participation provide an opportunity for a novel approach that "kills two birds with one stone."

A key deficiency of existing systems is their lack of connection to the "healthcare transaction flow" through which users purchase health-related goods and services. If a BSA system could insert itself into this transaction flow, and provide users with economic incentives (credit, discounts, etc.) based upon the nature and extent of their interaction with the system, such additional economic incentives would complete a feedback loop that reduces healthcare costs as a means of encouraging active user participation, which in turn enhances overall wellness.

Not surprisingly, some financial services companies have delved into the healthcare sector. For example, Citigroup's "Money$^2$ for Health" project, is a payment processing and reconciliation system (online automated "spreadsheet" with integrated payment transaction capability) that allows consumers to maintain payment history and make payments from one portal to all healthcare providers and insurance companies registered on the site. But, this project neither includes nor suggests any connection to a BSA system, much less any reliance on patients' interaction with such a system as a factor in assessing benefits provided to patients, such as credit and discounts on the purchase of health-related goods and services.

While financial services companies such as Klarna (a European mobile payment provider based in Sweden), have experimented with "micro credit" and various other credit-assessment techniques (see, e.g., published patent applications WO/2013131971 and US/2011030738), no such company has even suggested targeting credit-assessment techniques at purchases of health-related goods and services, much less basing credit assessments on users' interaction with a BSA system.

Thus, there remains a need for a BSA system that addresses the problems of high healthcare costs and inadequate patient participation by enabling users to purchase health-related goods and services via their user accounts, and automatically and dynamically providing economic incentives to users based upon the nature and extent of their interaction with the system.

SUMMARY

To address the above-referenced problems, the present invention includes various embodiments of a BSA system that facilitates the collection of user related data, including their relevant activities, on a continual basis, integrates such data with other pertinent personal and aggregate information, and guides users toward behaviors that help achieve system level and user specific goals such as enhancement of the user's overall wellness. The BSA system applies to any sphere of user activity, such as entertainment, travel or overall lifestyle, commercial transactions etc., but is described herein with regard to its application in healthcare and wellness support. The BSA system enables users to purchase health-related goods and services (directly using the system, as well as indirectly via their user accounts), while providing credit, discounts and other economic benefits in connection with such purchases that are determined dynamically based upon the nature and extent of users' interaction with the system.

In one embodiment, the BSA system continually monitors and analyzes users' behavioral interactions with the system. This health-related behavior includes various factors relating to the nature and frequency of information the user provides to and receives from the system (e.g., queries and responses, symptoms and other shared health status information, content browsed, games played, interactions with other users on social networks, health-related purchases, and shared third-party lab results, fitness data and other external information, among other factors).

In one embodiment, users accumulate and lose points, based upon the nature and frequency of virtually all of these direct and indirect interactions with the system. Various algorithms are employed to convert this raw data into particular attributes of credit levels, discounts for specific health-related products and services, and other benefits.

A Benefits Engine assesses the appropriate amount of credit (as well as discounts and other promotions) to offer users based upon this multi-dimensional data. Over time, the Benefits Engine may raise or lower a user's credit level (credit limit, interest rate, appropriateness of particular purchases, etc.) and reward the user with particular discounts, based upon dynamic changes in the user's behavior, as well as standard financial profile and transactional behavior data (including timeliness of payments to the BSA system provider).

The BSA system facilitates this dynamic feedback process by continually monitoring user interaction and medical and financial behavior, which results in dynamic adjustments to their credit levels and offers of discounts and other promotions, which in turn incentivizes users to continue participating in the process (thereby modifying their system interactions and behavior, and thus perpetuating this feedback loop). As a result, users are incentivized to actively participate in the process and thereby enhance their wellness while reducing healthcare costs.

For example, if a user frequently browses or searches for information relating to a particular nutritional supplement, and provides periodic information relating to their usage of that supplement over time, this behavior suggests that the user places a relatively high value on that supplement, perhaps justifying a discount on that supplement (or on related products and services). Moreover, the user may in fact value that supplement over other non-healthcare-related items (e.g., a cable bill), perhaps justifying a higher credit limit in connection with purchases of health-related goods and services via their user account.

The credit assessment process of the present invention involves consideration not only of standard financial profile and transactional behavior data, but also of specific health-related behavioral data, which is particularly relevant given that user credit is targeted at financing purchases of health-related goods and services. In one embodiment, aggregate behavior of others (including other BSA system users, or a correlated subset of such users) is also considered in the credit-assessment process, as well as in the determination of which discounts, promotions or other benefits (including targeted advertisements) are offered to particular users.

Rather than address merely a single facet of a user's health (fitness, prescription medications, test results, discrete illness or injury, etc.), the BSA system of the present invention provides a holistic approach that engages the user in interaction on a frequent basis over time. In one embodiment, the system provides a graphical, voice-enabled and touch-based user interface on mobile as well as desktop and other online platforms, aided by a natural language engine and back-end health expert system, that guides users through a myriad of health concerns and queries. The system provides personalized suggestions relating to each user's personal health condition and wellness goals, as well as reminders of medical appointments and medication schedules and real-time notifications of location-specific general health concerns (such as the spread of an infectious disease in a user's geographic area).

The system processes user voice input and queries and displays responses utilizing various media (voice, text, graphics, animation, video, etc.) that prompt users for additional information on an "as-needed" basis, rather than requiring users to fill out long forms and provide data that is not relevant at the time. Users provide proxies for external resources, such as pharmacies, labs, medical centers and retail providers of health-related goods and services. In one embodiment, the system notifies emergency contacts provided by users in the event of an emergency explicitly identified by a user or inferred from user interaction with the system (e.g., data from a wearable heart monitor).

User profiles are maintained and updated dynamically, and are available to users on a secure basis at all times. A frequent "active check-in" process enables the system to monitor user health by listening to, recording and categorizing any health-related information users provide. Such information includes daily replies to check-in prompts (e.g., "How did you sleep last night?" or "How is the pain in your neck?"), volunteered symptoms (e.g., "Now my arm hurts as well as my neck") and other health status factors relevant to their physical and mental state, as well as information obtained from wearable and other user monitors and other external sources (via user proxies where necessary—e.g., lab results following a blood test).

The system provides personalized responses, utilizing its expert system and user profiles (including external data), as well as aggregate third-party data. In one embodiment, the system provides an immediate response upon detecting a trend or concern based on information provided by a user. Such a response might include a recommendation to contact a particular doctor, a warning to avoid certain behavior, or a follow-up question regarding other potential symptoms. Less time-sensitive personalized recommendations include providers of health-related goods and services (including medical specialists) as well as "best practices" relating, for example, to particular medications, nutritional supplements, food, or fitness schedules. The expert system "learns" over time, providing more accurate and personalized information as a result of increasing experience with individual users and correlation of aggregate user and other external data over time.

In another embodiment, the system maintains a personalized calendar and diary based on various user data relating, for example, to exercise routines, medications, doctor appointments and other scheduled behaviors. The system employs this calendar to notify users when such events are imminent, and also to prompt users when a concern is detected (e.g., asking whether a daily medication was missed based on a recurring symptom).

The system encourages continuing and active user participation via an engaging interface, including health-related and other games and content designed to inform, entertain and motivate users (and from which the system infers user interests). In addition, the system detects patterns and events (e.g., from analyzing and correlating user profiles, external data and general medical information) and dynamically generates anonymized wellness social networks and initiates connections among users implicated by such patterns and events (e.g., a group of users sharing a particular set of symptoms or medical condition, or an interest in a particular health-related subject). In one embodiment, the system also offers premium services, such as real-time online consultations with medical professionals or less immediate recommendations based on a remote review of a user's health profile.

DETAILED DESCRIPTION

"Health" is generally defined and measured as a level of functional or metabolic efficiency of a living organism. In humans, it is a general condition of a person's body and mind. "Healthcare" involves the diagnosis, treatment and prevention of disease, illness, injury and other physical and mental impairments.

Yet, healthcare has proven to be extraordinarily expensive and ineffective. Access to doctors and other medical professionals is often both time and cost prohibitive, and effective personalized preventive wellness techniques have proven elusive, even in our highly technological age, despite the existence of various "wellness incentive programs" offered by governments, insurers, private employers and other organizations to promote health, encourage healthy behavior and discourage unhealthy behavior.

In accordance with the present invention, various embodiments of a novel architecture and methods are disclosed for a BSA system that continually monitors and analyzes user interaction and medical and financial behavior over time and dynamically adjusts user benefits (including credit assessments and promotional discounts) based on such monitored data. Such personalized benefits are implemented as an integral part of a dynamic feedback mechanism that incentivizes continued user interaction with the BSA system, including user purchases of health-related goods and services. As a result, users are incentivized to actively participate in the process and thereby enhance their wellness while reducing healthcare costs.

Figure 1:
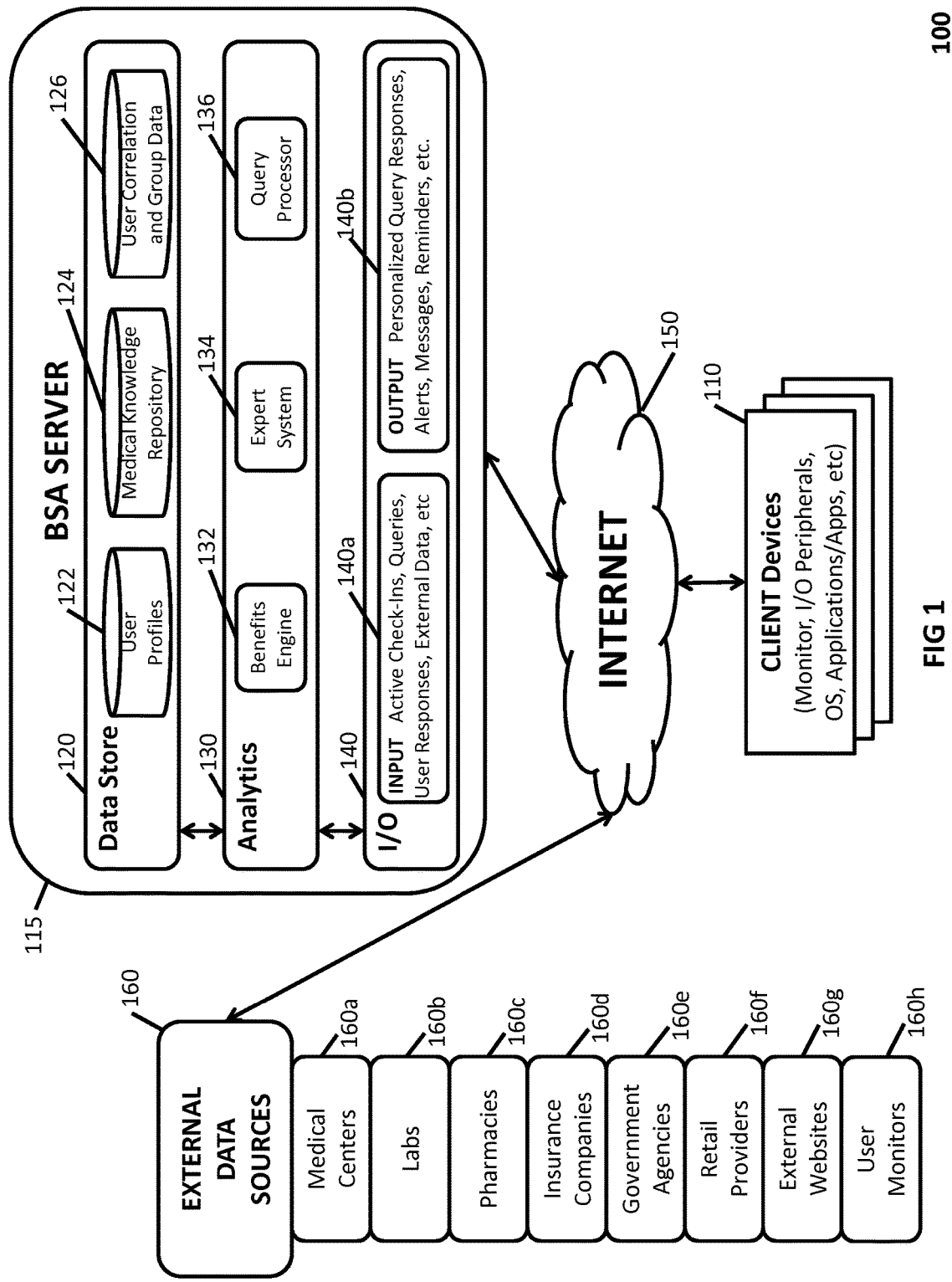
FIG. 1 is a block diagram illustrating an embodiment of a system architecture of the present invention.

FIG. 1 illustrates an embodiment of a system architecture of a BSA system 100 of the present invention. Users employ various Client Devices 110 to connect (in this embodiment, via the Internet 150) to a BSA Server 115 that functions as an ever-present user-friendly interactive behavioral support agent. In other embodiments, system components may be interconnected via LAN, WAN or other network connections. Even while users are not interacting with BSA server 115 via their Client Devices 110, BSA Server 115 may interact with various External Data Sources 160 to exchange information that can be employed in subsequent user interactions (with third-party organizations and physical devices as well as with BSA server 115).

It should be emphasized that the functionality embodied in BSA Server 115 and Client Devices 110 can be allocated among various different hardware and software components. For example, BSA Server 115 could be implemented as a single server computer or as multiple interconnected computers. The connectivity among the various components of BSA system 100 can also vary in other embodiments. For example, certain External Data Sources 160 may connect directly to Client Devices 110, while others may connect to BSA Server 115.

Moreover, the distribution of "client-server" functionality between BSA Server 115 and Client Devices 110 can range from a "dumb client" implementation (in which Client Devices 110 merely display information and transmit user input to BSA Server 115) to "smarter client" scenarios in which client applications or smartphone "apps" implement some or all of the functionality of BSA Server 115 illustrated in FIG. 1. Whether functionality is implemented in hardware or software, or in a client or server, is a design decision. The software components described herein (as well as user and other data) can be embodied in various physical storage media (i.e., memory), including non-transitory computer-accessible storage media.

Client Devices 110 can include server, desktop, laptop and mobile devices, such as smartphones, with various hardware peripherals, such as monitors and touchscreens, keyboards, mice and touchpads, among others. Software in Client Devices 110 can include operating systems and applications, as well as smartphone "apps." In one embodiment, Client Devices 110 utilize a web browser client to communicate with BSA Server 115, while other embodiments employ one or more smartphone apps. In another embodiment, Client Devices 110 employ a user-friendly graphical, voice-enabled and touch-based interface that facilitates an engaging interactive experience, enhanced via a natural language engine, as discussed in greater detail below).

Users of Client Devices 110 may utilize health-related wearable and other user monitoring devices to track various aspects of their health (heart rate, blood pressure, etc.). Such monitoring devices can, in other embodiments, be present on Client Devices 110 (e.g., smartphone GPS, cameras and other hardware) and can communicate directly with BSA Server 115. User Monitors 160h are but one example of the External Data Sources 160 that exchange information with BSA Server 115 in the background, regardless of whether users are interacting with BSA server 115 via their Client Devices 110. Examples of other External Data Sources 160 include Medical Centers 160a (e.g., notes, schedules, diagnoses, billing and other information from hospitals, doctors' offices and outpatient treatment and surgical centers, among others), Labs 160b (e.g., for blood tests, MRIs, etc.), Pharmacies 160c (e.g., for prescription drug billing and other information, as well as other health-related products), Insurance Companies 160d (e.g., for policy, claim and billing information), Government Agencies 160e (e.g., for medical benefit payments and related information), Retail Providers 160f (e.g., information regarding health-related products and services from third-party retail websites and portals, as well as billing and payment information for such products and services), and External Websites 160g (e.g., an external social network or a personalized website hosting an exercise regimen or other health-related information that is tracked externally but shared with BSA system 100).

These External Data Sources may be accessed via external "proxies" or standard APIs for exchanging information with software running on other devices, such as computers (e.g., BSA Server 115) or smartphones (e.g., Client Devices 110). Such external data may be "pushed" to BSA Server 115 whenever an update occurs (e.g., when a prescription is refilled) or "pulled" by BSA Server 115 via periodic polling (e.g., a daily check of a website for updated information).

The components of BSA Server 115 can be roughly classified into three categories or layers of functionality. Note that this is a conceptual construct, and that certain functionality may be implemented across multiple of these layers, as well as multiple different computers or other devices, including Client Devices 110 in some embodiments.

One such layer is the Data Store 120, which includes various databases for storing information that can be exchanged with other components of BSA system 100. One key database maintains User Profiles 122, which include a vast array of personalized information specific to each user. In other embodiments, User Profiles 122 may be implemented as multiple distinct but interconnected databases.

User Profiles 122 include standard medical profile data, such as name, age and other identifying information, as well as information relating to health insurance and doctors, medical history and credit history and so forth. In addition to this standard profile information, User Profiles 122 may also include data relating to user interaction with BSA system 100 and with External Data Sources 160 that exchange information with BSA Server 115.

Such information includes direct "substantive" data from both External Data Sources 160 (links and APIs, lab results, monitored fitness data, purchases of health-related goods and services, etc.) and from user interactions with BSA system 100 (e.g. any combination of symptoms, health status, sleep patterns, activities performed, queries, medications, premium and other requested services, direct purchases of health-related goods and services, participation in social networks, games played etc.). In some embodiments, the BSA system 100 would encourage regular reporting or check-in of symptoms and health status by users and such data is stored in User Profiles 122. In some embodiments, all user interaction with BSA system 100 including check-in of symptoms is treated as an interactive process akin to a query, requiring responses and follow-up by both user and BSA system 100 and the entire interaction is stored in User Profiles 122.

User Profiles 122 also include indirect "procedural" interaction data and metadata, such as the nature and frequency of interactions with both BSA system 100 and External Data Sources 160 (e.g., number and frequency of purchases of health-related goods and services, frequency of active check-ins or reporting of symptoms, number of queries posed, overall time and quality of interaction with games and other system components, specific games played and scores achieved, calendared data for medications and workout schedules, areas browsed and clicked on, participation with other users via system-generated social networks, etc.).

Metadata generated by other components of BSA system 100 and stored in User Profiles 122 include benefits data (credit limits and interest rates, product and service discounts, and various multidimensional behavioral metrics) as well as aggregate data correlated from patterns detected across other users and third parties (e.g., potential diagnoses based on similar symptoms across a spectrum of other users or recent medical findings).

In short, User Profiles 122 include virtually all personalized data collected and maintained by BSA system 100 that is specific to each user, as well as various metrics and annotations derived from such data (collectively, as well as individually). User Profiles 122 are updated dynamically on a continual basis as users interact with BSA system 100 and as information is exchanged with External Data Sources 160.

Data Store 120 also includes, in one embodiment, a Medical Knowledge Repository 124 that constitutes a comprehensive collection of generic medical knowledge (not personalized to specific individuals) that can be analyzed by other components of BSA system 100 and used for a variety of purposes, such as updating User Profiles 122 based on detected patterns among aggregate data and/or recent medical findings (e.g., side effects of medications), responding to specific user queries, alerting users to recent infectious outbreaks, among a variety of other functions. In another embodiment, External Data Sources 160 include non-personalized generic medical data from various organizations and third-party websites that provide updates to BSA Server 115 as new information is made available.

Another component of Data Store 120 is User Correlation and Group Data 126, which includes aggregate data (generated and maintained by Expert System 134 in this embodiment) that is not targeted at any specific user, but represents detected patterns across users (as well as other third parties) based on information maintained in other databases of Data Store 120, such as Medical Knowledge Repository 124. For example, BSA system 100 might detect (from an analysis of recent updates to User Profiles 122), a pattern of symptoms reported by users between the ages of 50-60 from California and Arizona, which leads to a hypothesis (supported by general medical information maintained in Medical Knowledge Repository 124, or relying upon patterns first detected by BSA system 100) that an infectious disease, to which individuals of that age group are particularly susceptible, may be spreading in that area.

Information relating to these correlations among aggregate data is maintained and updated dynamically in User Correlation and Group Data 126, which is utilized by Expert System 134 to trigger updates to User Profiles 122 and Medical Knowledge Repository 124, as well as Output 144 to users. Updates to User Profile 122 may include annotations for future use such as potential caution if user starts certain new medications that may have adverse effects based on their existing profile data. Updates to Medical Knowledge Repository 124 may similarly include information on heretofore unknown or unreported drug-drug or drug-food interactions, or adverse or beneficial effects of medications, supplements, therapies etc. depending on particular health or lifestyle characteristics. Triggers to Output 144 may for example be an alert targeted at a subset of potentially affected users. In one embodiment, a more limited subset of users may receive more detailed and personalized alerts (e.g., based upon the specific symptoms they have already reported). Such alerts could include, for example, a more detailed analysis of a potential condition, a recommendation to contact a specific specialist doctor (or a user's personal doctor stored in User Profiles 122), a connection to other users with similar symptoms to facilitate sharing of information and possible treatments as well as recommendations for preventive or therapeutic actions (e.g., icing your knee, refraining from strenuous activity or using a particular drug or product). Various other patterns and correlations of aggregate data (e.g., potentially dangerous side effects of a particular drug or combination of drugs, or effective treatments, products or services) are made possible by the availability of dynamically updated detailed health profiles. Moreover, the accuracy, scope and overall value of these correlations improves as more users interact more frequently with BSA system 100 over time.

The processing and analysis of the data maintained in Data Store 120 is performed by the Analytics 130 layer of functionality in BSA Server 115. As noted above, these layers may be combined or further segmented, the data may be pushed or pulled by various layers of BSA Server 115, and some or all of this functionality can, in other embodiments, be performed by Client Devices 110.

Benefits Engine 132 (explained in greater detail below with reference to FIG. 7) implements a dynamic feedback mechanism which is driven by user interaction with BSA system 100 and with External Data Sources 160. BSA system 100 monitors these interactive and data update "events" (relying upon and updating Data Store 120 as necessary) and provides them to Benefits Engine 132 which quantifies them and dynamically generates various personalized user benefits (credit, discounts, etc.), which in turn incentivizes users to further participate in their own wellness by continuing to interact (and perhaps increasing the nature and scope of their level of interaction) with BSA system 100.

Users are incentivized by the benefits provided by Benefits Engine 132 to finance and purchase health-related goods and services via their user accounts (in some cases discounted for all or a selected subset of users), and to interact with BSA system 100 more extensively, e.g., providing daily check-ins, initiating more queries and following resulting suggestions. This continued interaction is then fed back to Benefits Engine 132 to complete the feedback loop and generate further user benefits. As a result, users are guided toward behavior that enhances their wellness while reducing healthcare costs.

The manner in which these interactive and data update events are monitored by BSA system 100 is explained in greater detail below with respect to FIGS. 2 and 3. The detailed operation of Benefits Engine 132, including the generation and quantification of multidimensional metric values, and transformation into specific assessments of credit, discounts and other personalized user benefits, is described below with reference to FIG. 7.

Another Analytics 130 component is Expert System 134, which is responsible for much of the intelligence underlying the interactive behavior of BSA system 100. Expert System 134 relies upon (and maintains) dynamically updated information in Data Store 120 to perform various functions, such as responding to user queries, detecting and correlating patterns among aggregate data which are employed to generate user suggestions and alerts, and engaging in "intelligent" interactions with users that (due to the extensive amount of personalized and aggregate data available to Expert System 134) go beyond merely simulating a conversation with a medical professional. It should be noted that Expert System 134 is a "learning" system in that its capabilities improve over time as more information is obtained from more users on a consistent (and perhaps more frequent) basis.

In one embodiment, Query Processor 136 parses and analyzes user queries and converts them into a format compatible with Expert System 134 and prepares and provides responses via Output 144. In other embodiments, the functionality of Query Processor 136 is subsumed in Expert System 134. In yet other embodiments the Query Processor 136 or the Expert System 134 or portions thereof may be contained in Client Devices 110, which communicate as necessary with Expert System 134 on BSA Server 115.

In any event, certain queries (e.g., "What is diabetes?") might be categorized as a "general information" question requiring a simple lookup for general medical information stored in Medical Knowledge Repository 124 or external websites and databases, while other queries (e.g., "Why does my arm hurt after exercise?") might be categorized as a "symptom-related" question, possibly resulting in a follow-up question or graphic display seeking additional user input, e.g., identifying the part of the arm that hurts and specific conditions under which the symptom is triggered. Expert System 134 might also be invoked to analyze the user's prior medical history, stored in User Profiles 122, which in turn might lead to various requests for additional information before generating a personalized response (possible diagnosis, suggestion to see a particular doctor, etc.). These queries and responses are, in one embodiment, stored in User Profiles 122.

In this embodiment, direct interactions with users are implemented in a distinct I/O 140 layer, which provides an interface between users and other layers of BSA Server 115. In this embodiment, I/O 140 modules communicate directly with Analytics 130 modules, which read and write Data Store 120 databases. In another embodiment, I/O 140 modules access both Analytics 130 modules and Data Store 120 databases directly.

The functionality of I/O 140 modules is explained in greater detail below with reference to FIGS. 2 and 3. As a conceptual matter, these modules handle both Input 140*a* from users and Output 140*b* to users, employing various media (voice, text, graphics, animation, video, etc.). In one embodiment, however, I/O 140 modules are designed to implement highly interactive "conversations" that result in a great deal of overlap between input and output functionality.

In one embodiment, I/O 140 modules are the conduit through which BSA Server 115 interacts with users to implement a variety of different scenarios and provide various user services, including (among others):

Guiding users through their health concerns during frequent (e.g., daily) check-ins that may involve any combination of speech, typed text and graphical prompts (e.g., figures) for identifying symptoms and general physical and mental health status, as well as responses to and recommendations regarding user queries relating to medical conditions, fitness, nutrition, etc.

Monitoring users' direct and indirect behavioral interactions with the system, for use in providing a vast array of personalized user services, including those requiring correlations among aggregate user data Dynamically updating personalized user profiles including, for example, standard profile information, emergency and close family contacts, monitored behavioral interactions with the system and connections to users' external data sources (e.g., doctors, labs, pharmacies, insurance companies, wearable and other monitoring devices, GPS, etc.) via standard proxies and APIs with user-provided authentication credentials Providing personalized "best practices" treatment, nutrition and general healthcare suggestions to address specific user health issues and wellness goals (and even including, for example, localized suggestions using GPS coordinates to recommend nearby health-related facilities)

Reminding users of their medication schedules, medical appointments, and other calendared items, generating and maintaining a user calendar automatically based on direct and indirect user interactions with the system Generating and maintaining automatically personalized user diaries (e.g., of user exercise and other health-related routines) based on direct and indirect user interactions with the system Providing custom user alerts based on "real-time intelligence" (as well as location, weather and other environmental factors) regarding emergencies and related health events, such as the spread of a local infectious outbreak (in some cases relying upon users' current GPS coordinates), as well as personalized suggestions requiring, for example, a potential doctor visit Dynamically generating personalized and anonymized wellness social networks targeted at specific users sharing, for example, a particular set of symptoms or medical condition, or an interest in a particular medical subject or wellness goal (allowing group postings, real-time text and chat, and direct voice interaction, among other services)

Recommending medical specialists for user consultations

Providing instant and secure access to user medical records, including medical history, lab work, vaccinations, etc.

Offering premium paid services to users including, for example, real-time responses to health-related queries by medical professionals, or suggestions within a specific timeframe based on a remote review of health concerns by medical professionals Offering personalized credit financing for user purchases of health-related goods and services, based on their direct and indirect behavioral interactions with the system Offering personalized individual and group discounts and other promotions regarding user purchases of specific health-related goods and services, based on their direct and indirect behavioral interactions with the system (including, for example, providing anonymized health details for aggregate correlation Providing an engaging graphical, voice-enabled and touch-based user interface (supported by an intelligent back-end including an expert system that "learns" as more data is obtained over time) that includes games and other content to inform, educate and entertain users, as well as motivate them to continue to participate in further system interaction User Input 140*a* include data update events from External Data Sources 160, such as lab test results, prescription medication notifications, electronic receipts from retailers regarding purchases of health-related goods and services, user monitor data (e.g., results from a daily exercise routine, including distance traveled, heart rate and blood pressure or blood sugar data), and a wide variety of other types of data updates. Note that such data updates include not only externally-initiated events, but may also come in response to information queries initiated by other BSA Server 115 modules (e.g., a request for data from a heart monitor initiated by Expert System 134 in an effort to respond to a user-initiated query).

Other examples of user Input 140*a* include user queries and user responses, health status information and symptoms revealed during daily and ad hoc check-ins, and various other user interactions, such as browsing content, playing games, and participating in social conversations, as well as information collected directly from Client Devices 110 with or without active user participation. Virtually all such user Input 140*a* is monitored (as discussed in greater detail below) and stored in User Profiles 122 (e.g., for use in calculating personalized user benefits, such as credit and discounts), including metadata relating to the information provided, such as classifications of the type of information provided, time and frequency of particular types of interactions, among other metadata.

User Output 144, which is also monitored, includes personalized information generated by BSA Server 115 for users. Examples of such user Output 144 include responses to user queries and follow-up requests for additional information, general messages, product suggestions, specialist recommendations, alerts, reminders and other information presented to users employing various formats and media.

Figure 2:
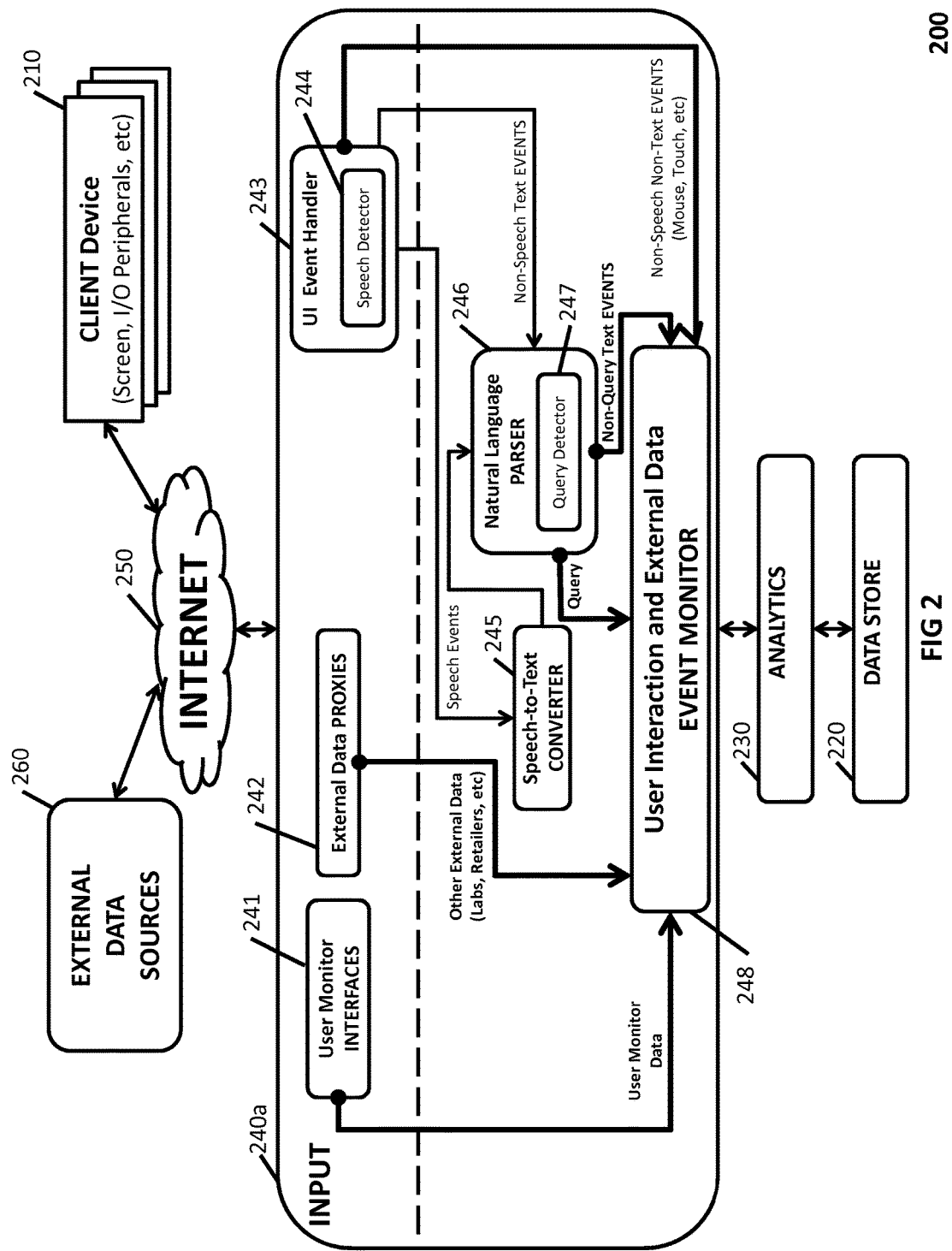
FIG. 2 is a block diagram illustrating an embodiment of additional components of an input-processing module of the present invention.

Turning to FIG. 2, block diagram 200 explores one embodiment of the input-processing functionality performed by BSA Server 115 (from FIG. 1) in greater detail, illustrating various key components. As noted above, this separation of input and output modules is conceptual, as there is a great deal of implementation overlap between input and output functionality.

Input-processing module 240*a* (140*a* from FIG. 1) obtains information, in one embodiment, via Internet 250 (150 from FIG. 1), from both External Data Sources 260 (160 from FIG. 1) and Client Devices 210 (110 from FIG. 1), and relies upon other BSA Server 115 modules, such as the various Analytics 230 (130 from FIG. 1) modules and Data Store 220 (120 from FIG. 1), to analyze and store this information. Various proxies and APIs, such as User Monitor Interfaces 241 and External Data Proxies 242, are employed to obtain information from External Data Sources 260. They then provide this external data to Event Monitor 248, as explained in greater detail below.

Other input events—i.e., user input obtained directly from users interacting with BSA system 100 via their Client Devices 210—require additional processing before being provided to Event Monitor 248. Such user input events are processed initially by UI Event Handler 243 which, in one embodiment, classifies these events into three categories.

UI Event Handler 243 employs Speech Detector 244 to identify speech events (i.e., user voice input), which it then provides to Speech-to-Text Converter 245, which converts that user voice input into text, which it then provides to Natural Language Parser 246. Remaining non-speech events fall into two categories—i.e., keyboard input (i.e., text) and other events, such as mouse or touch events.

UI Event Handler 243 provides these other (non-speech, non-text) events directly to Event Monitor 248, while providing the remaining non-speech text events to Natural Language parser 246, which parses the text (whether or not originally converted from user voice input), in one embodiment into a variety of distinct types of events before providing them to Event Monitor 248. For example, Natural Language parser 246 employs, in one embodiment, a Query Detector 247 to identify one of these event types as "queries", which are then provided to Event Monitor 248. Other non-query event types (e.g., query responses by users, symptoms, health status events, etc.) are separately provided to Event Monitor 248. In other embodiments, this functionality of identifying and classifying distinct event types, can be performed by Event Monitor 248, or various Analytics 230 modules on BSA Server 115.

Event Monitor 248, upon receiving these various different types of user input events originating from External Data Sources 260 and Client Devices 210, employs various Analytics 230 modules on BSA Server 115 to further process these events. In other embodiments Event Monitor 248, upon receiving these various different types of user input events may write them directly to Data Store 220 (120 in FIG. 1). In other embodiments, some or all of this analysis can be performed entirely on Client Devices 210 or on BSA Server 115.

In any event, such analysis, as noted above, may result in a variety of different actions including formulation of immediate responses to user queries, including follow-up queries to users, dynamic modifications of User Profiles 122, recommendations of potential user actions, such as visit to a particular doctor, dynamic generation of a social network connecting specific users, and a host of other actions and user "outputs" (discussed in FIG. 3 below). For example, in one embodiment, upon detecting patterns, events or other issues based on correlations among user and other internal and external data, Expert System 134 prompts users for further input and follows up with users over time until such issues are deemed resolved.

In the course of performing this analysis, these user input events, sometimes in combination, are classified into various different categories, including (among others):

Data from User Monitors and related devices

Visits to Doctors, Labs, Pharmacies, Retailers, Affiliated Websites, etc

Contractual health-related Information from Insurance companies, Government Agencies, etc.

Queries

Reports of Symptoms, Health Status, Nutrition and Exercise regimens, etc.

Interactions with other users and third parties (e.g., internal and external Social Networks)

Games-related data

Purchases (internally and externally) of health-related goods and services via user accounts Metadata relating to various user interactions regarding the nature and frequency of user input events (e.g., number and frequency of check-ins, time spent browsing particular content, number and types of symptoms or health status reports, and various other types of metadata)

Figure 3:
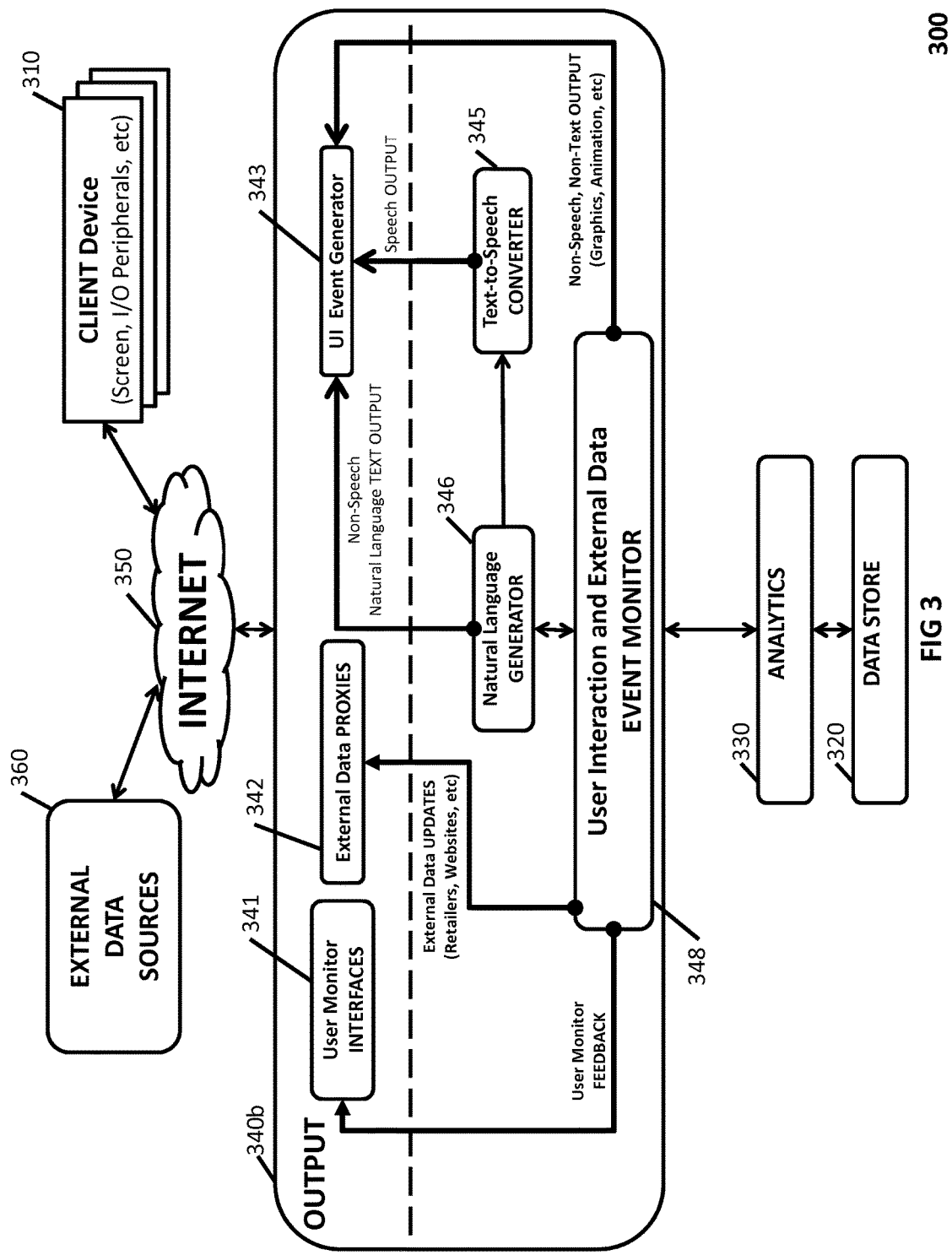
FIG. 3 is a block diagram illustrating an embodiment of additional components of an output-processing module of the present invention.

Turning to FIG. 3, block diagram 300 explores one embodiment of the output-processing functionality performed by BSA Server 115 in greater detail, illustrating various components. As noted above, in one embodiment, Output-processing module 340*b* (140*b* from FIG. 1) receives different types of output events, via Event Monitor 348 (248 from FIG. 2) generated by various Analytics 330 (230 from FIGS. 2 and 130 from FIG. 1) modules on BSA Server 115, relying upon Data Store 320 (220 from FIGS. 2 and 120 from FIG. 1).

Such output events are ultimately communicated, via Internet 350 (250 from FIGS. 2 and 150 from FIG. 1) to both External Data Sources 360 (e.g., ordering a prescription refill) and Client Devices 310 (e.g., responding to a user query or other input, or initiated by BSA Server 115). Initially, however, such output events (in one embodiment) are forwarded to and processed by Event Monitor 348.

For example, feedback generated for user monitors (e.g., to initiate an immediate heart rate test) is forwarded to the appropriate device via User Monitor Interfaces 341 (241 from FIG. 2). External data updates (e.g., ordering a prescription refill, requesting a doctor appointment, etc.) are forwarded to External Data Proxies 342 (External Data Proxies 242 from FIG. 2) for transmission to the appropriate one of the External Data Sources 360 (260 from FIGS. 2 and 160 from FIG. 1).

Remaining output events, however, may require additional processing before being provided to users via their Client Devices 310 (210 from FIGS. 2 and 110 from FIG. 1).

Note that such output events may be presented to users employing various different media (text, speech, graphics, animation, video, etc.).

For example, textual and spoken output is first processed by Natural Language Generator 346 (same module, in one embodiment, as Natural Language parser 246 from FIG. 2), which converts the output event into a natural-language textual message (e.g., "I think you should make an appointment with your orthopedist, Dr. Smith"). That textual message can be forwarded directly to UI Event Generator 343 (for display to users via their Client Devices 310), or first converted to speech, via Text-to-Speech Converter 345 (same module, in one embodiment, as Speech-to-Text Converter 245 in FIG. 2), and then forwarded to UI Event Generator 343 (same module, in one embodiment, as UI Event Handler 243 from FIG. 2) for delivery to users via the speakers of Client Devices 310. In one embodiment, natural language output is delivered to users as both speech and text.

To illustrate the type of interactive communication afforded by BSA system 100, consider the following scenarios of daily user "check-ins" in which all interaction is recorded (including, for example, time and date) and logged in User Profiles 122:

Scenario 1
[User] "My knee is hurting"
[System] "Which knee?"
[User] "The right"
[System] "When did it start?"
[User] "Bothering me since this morning"
[System] "How did you injure it?"
[User] "Don't remember"
[System] "You were at the bowling alley last night. Do you think you sprained it there?"
[User] "I think so"
[System] "Is there any swelling in the knee?"
[User] "Yes"
[System] "Is it wobbly and moving from side to side?"
[User] "Yes"
[System] "You need to see Dr. Smith. I'll connect you to make an appointment."
Scenario 2
[User] "I am feeling lightheaded"
[System] "Did you eat an apple with your NewBPDrug?"
[User] "Yes"
[System] "Many patients are seeing the same symptoms. It seems to pass after about 20 minutes. I'll send a note to your doctor. Next time remember not to eat an apple with your NewBPDrug. Let's talk again in 20 minutes."
[System] [20 minutes later; if no check-in from user] "Are you still feeling lightheaded?"
[User] "Much better but not fully gone."
[System] "That's a good sign. Let's check again in 15 minutes"
[System] [15 minutes later; if no check-in from user] "Are you still lightheaded?"
[User] "No"
[System] "I'll make a note that it may take you longer than usual to recover from the symptoms."

This iteration of input and output events illustrated in FIGS. 2 and 3 forms the basis for the various types of personalized interactions between BSA Server 115 and both users (via their Client Devices 310) and their External Data Sources 360. As noted above, virtually all of these personalized interactions are monitored (by Event Monitor 248 in FIG. 2 for input events, illustrated as Event Monitor 348 in FIG. 3 for output events) for use by various other components of BSA system 100.

Figure 4:
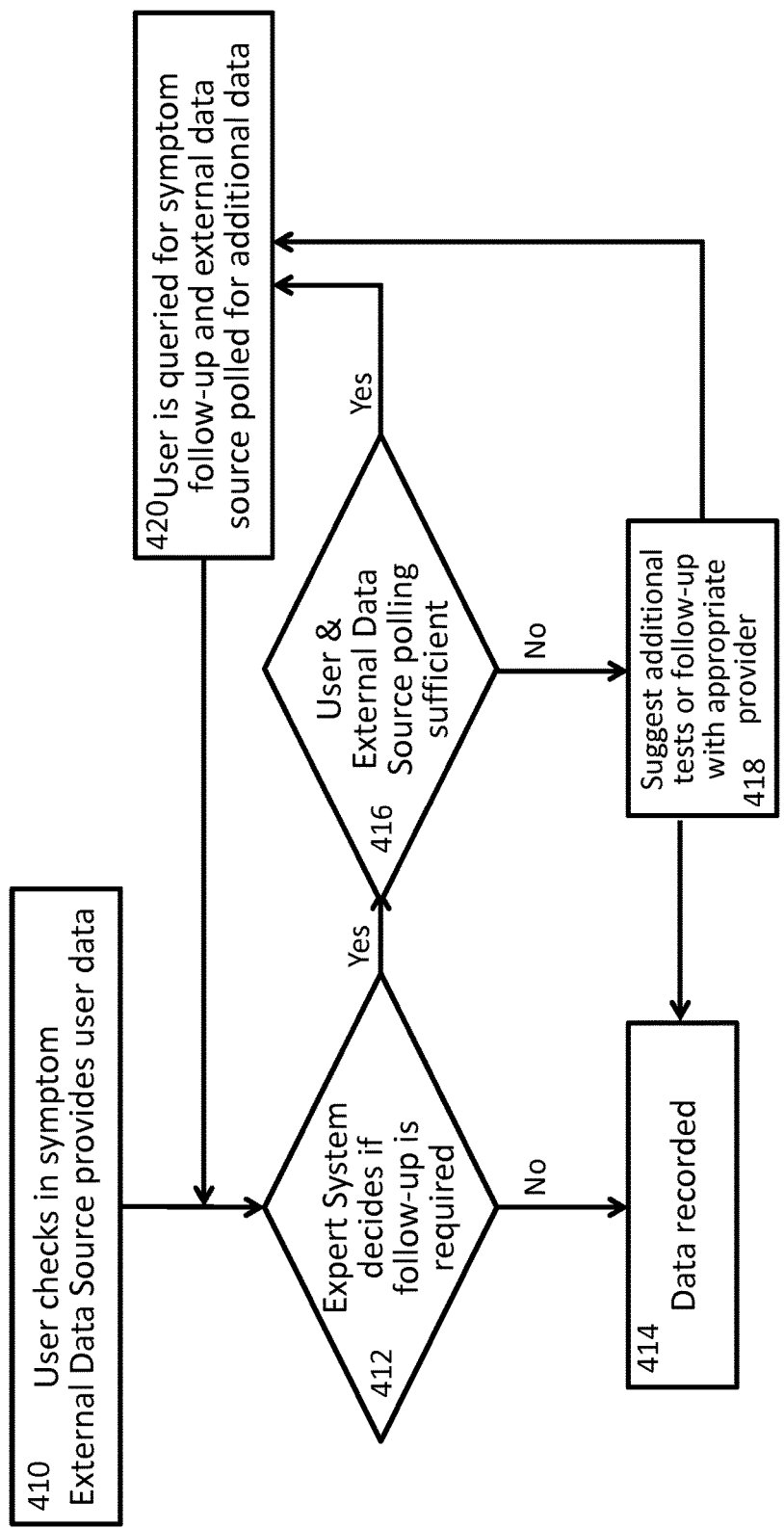
FIG. 4 is a flow chart illustrating an embodiment of a dynamic monitoring and follow-up of user symptoms facilitated by an expert system module of the present invention.

FIG. 4 illustrates one embodiment of a process 400 in which BSA system 100 determines, as information is received relating to a user's medical condition, that a follow-up course of action is warranted. For example, BSA system 100 may prompt the user with additional queries, recommend additional tests, suggest that the user contact a specialist, or pursue various other courses of action warranted by the vast array of information made available to BSA system 100 from the user, as well as from other users and third-party data sources.

In this embodiment, at any given point in time (e.g., during a daily check-in), a user provides BSA system 100, in step 410, with information, such as a particular symptom. Alternatively, BSA system 100 may receive data (e.g., a lab result) from External Data Sources 160. In any event, such information is eventually processed by Expert System 134, which determines, in step 412, whether a follow-up course of action is warranted.

In most situations, no follow-up is necessary, and the information is simply recorded in Data Store 120 (including User Profiles 122), at which point process 400 terminates. Note, however, that process 400 resumes each time BSA system 100 receives information from users, whether directly or indirectly via External Data Sources 160.

Whenever a follow-up course of action is warranted in step 412, then Expert System 134 determines, in step 416, whether requests for additional information from the user (whether via direct queries and/or prompts, or indirect access to External Data Sources 160) will be sufficient, or whether additional tests or referral to a doctor or other healthcare provider are also required.

If additional user information will be sufficient, BSA system 100, in step 420, queries the user directly (e.g., prompting for additional status on reported symptoms over a particular period of time) and/or polls External Data Sources 160 for additional information (e.g., monitoring the user's blood pressure over time). Upon receiving such additional information, process 400 returns to step 412 for reevaluation by Expert System 134. Note that this "loop" may repeat for multiple iterations, in some cases requiring additional information from users, and in others requiring additional tests or medical intervention.

If Expert System 134 determines, in step 416, that additional tests or medical intervention are needed, then such recommendations are communicated to the user in step 418 and recorded in Data Store 120 (including User Profiles 122). In this case, however, process 400 does not necessarily terminate. Additional information from the user may also be required in step 420. For example, BSA system 100 may, in addition to recommending that the user contact a particular specialist, also prompt the user for additional information regarding related symptoms. In any event, process 400 may eventually resume, at step 410, after the user follows up with particular recommendations and, for example, receives test results and other information such as notes from the recommended doctor.

As is apparent from the above description of FIG. 4, process 400 is an ongoing process designed to "intervene" (with recommendations to users or prompts for additional information) whenever Expert System 134 deems that an additional follow-up course of actions is warranted. Though involved in this process by providing information (e.g., via daily check-ins and indirectly via External Data Sources 160), users need not initiate the process, and in many cases will not even be aware that such intervention is warranted until prompted by BSA system 100.

Figure 5:
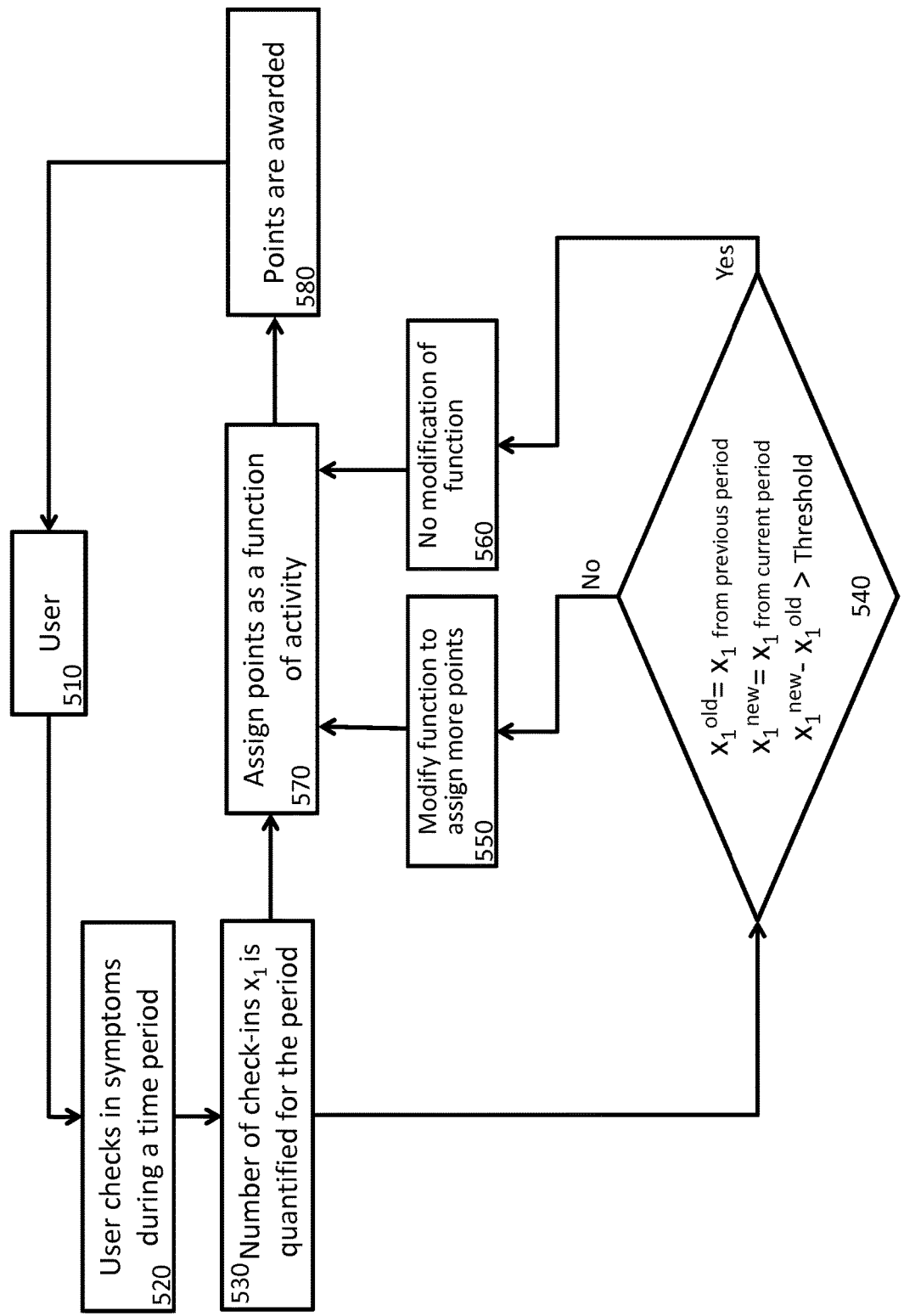
FIG. 5 is a flow chart illustrating an embodiment of a dynamic feed-back loop for providing certain benefits to user by a benefits module of the present invention.

FIG. 5 illustrates one embodiment of a process 500 in which BSA system 100 motivates and encourages users to use the system via changes in awarding points. In one embodiment, this functionality is implemented via Benefits Engine 132 in FIG. 1.

In one embodiment, module 520 (as an example aspect of modules further described in 780 in FIG. 7) receives and stores all user check-ins during a given time period directly from user via Event Monitor 248 of FIG. 2 (348 in FIGS. 3 and 748 in FIG. 7) while in another embodiment module 520 may retrieve this data from User Profile 122 in FIG. 1, and subsequently makes this data available to module 530.

Figure 7:
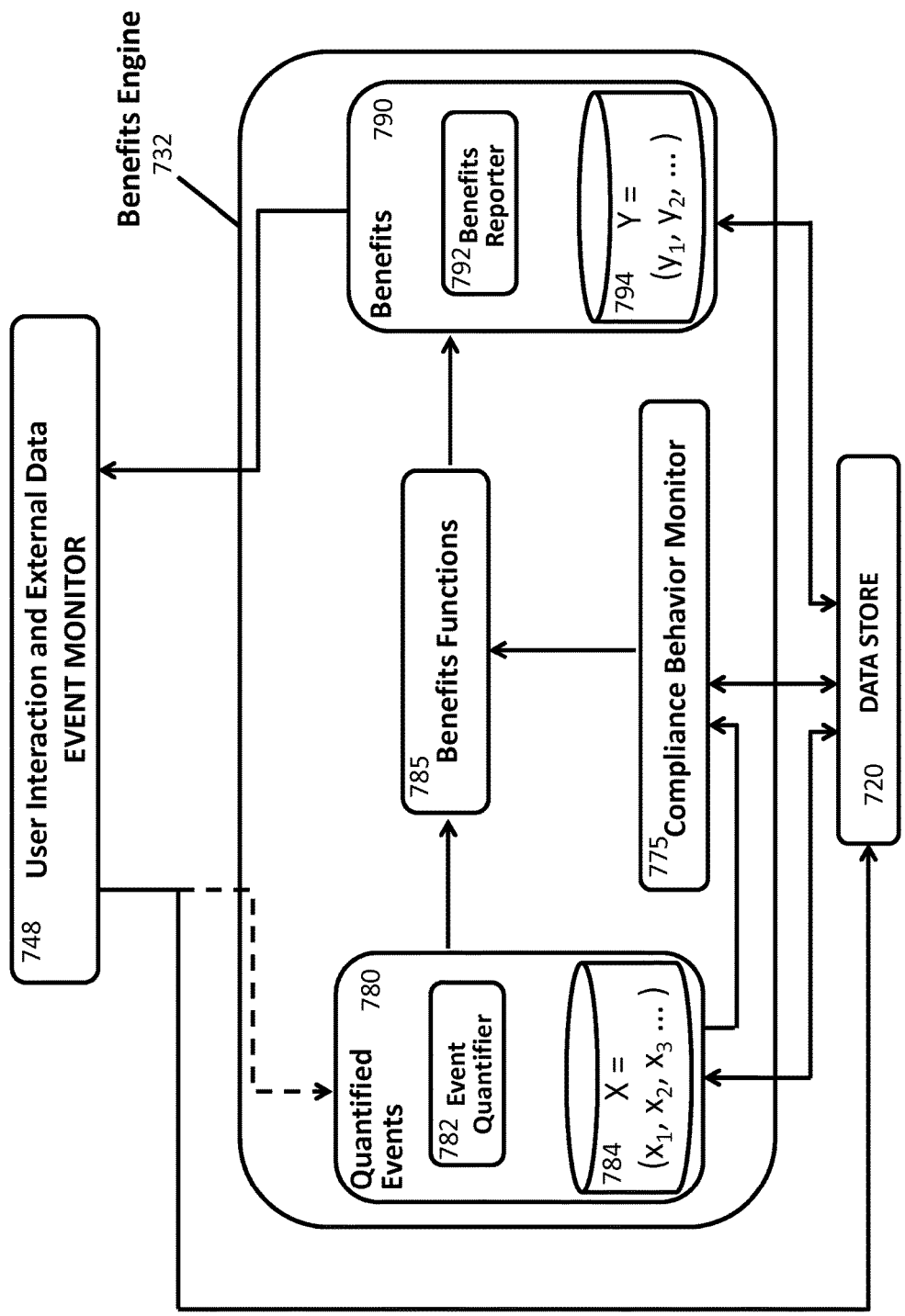
FIG. 7 is block diagram illustrating a dynamic feedback loop of the present invention between user behavior and economic benefits and other incentives.
Figure 8:
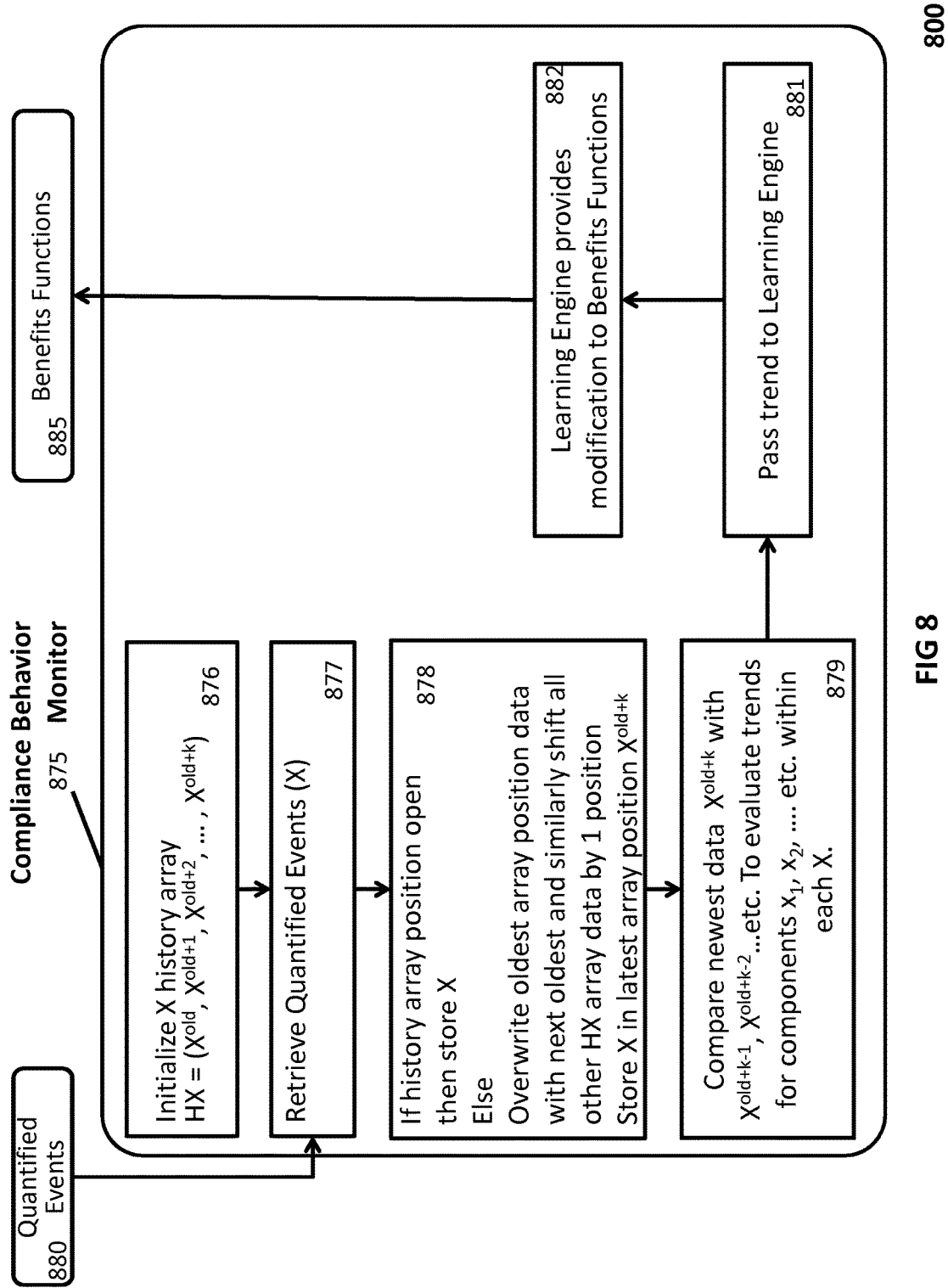
FIG. 8 is a flow chart illustrating an embodiment of dynamic monitoring of user behavior and adjustment of benefits provide to said user in an attempt to encourage or reinforce desirable user behavior.

In one embodiment, in module 530, the number of symptom check-ins during a week, say, may be recorded as a quantified user related data variable $x_1$ (as an example aspect of module(s) further described in 784 of FIG. 7). Module 570 utilizes a function (as an example of what is described below in Benefit Function 785 of FIG. 7) that uses $x_1$ (in some embodiments in combination with other user related data or other users' data) to calculate points to be awarded to user (such points may be one of the benefits as described in the benefits module 790). In some embodiments such points may be redeemable for specified discounts on products purchased via user accounts. These points motivate the user to continue checking in symptoms on a frequent basis. In one embodiment module 540 (as an example aspect of module(s) further described in Compliance Behavior Monitor 775 in FIGS. 7 and 875 in FIG. 8) may receive and maintain historical record of $x_1$ values and compare for instance the value of $x_1$ from the current period ($x_1^{new}$) with that from the previous period ($x_1^{old}$) to determine if the increase in the number of symptom check-ins is above a certain threshold. If not, then module 550 may modify the point assignment function in module 570 to assign more points for a given number of symptom check-ins to motivate user to use the system. If the threshold in module 540 is exceeded then module 560 may not modify the point assignment function in module 570. In other embodiments the behavior of modules 550 and 560 may be different, even reversed to penalize the user for not using the system.

As is apparent from the above description of FIG. 5, process 500 is an ongoing process designed to "intervene" (by modifying points rewards to users) whenever Benefits Engine 132 deems that necessary. Though involved in this process by providing information (e.g., via symptom check-ins), users need not initiate the process, and in many cases will be gently nudged by the BSA system 100 towards modifying their behavior towards achieving desired system-wide as well as user specific goals and outcomes.

Figure 6:
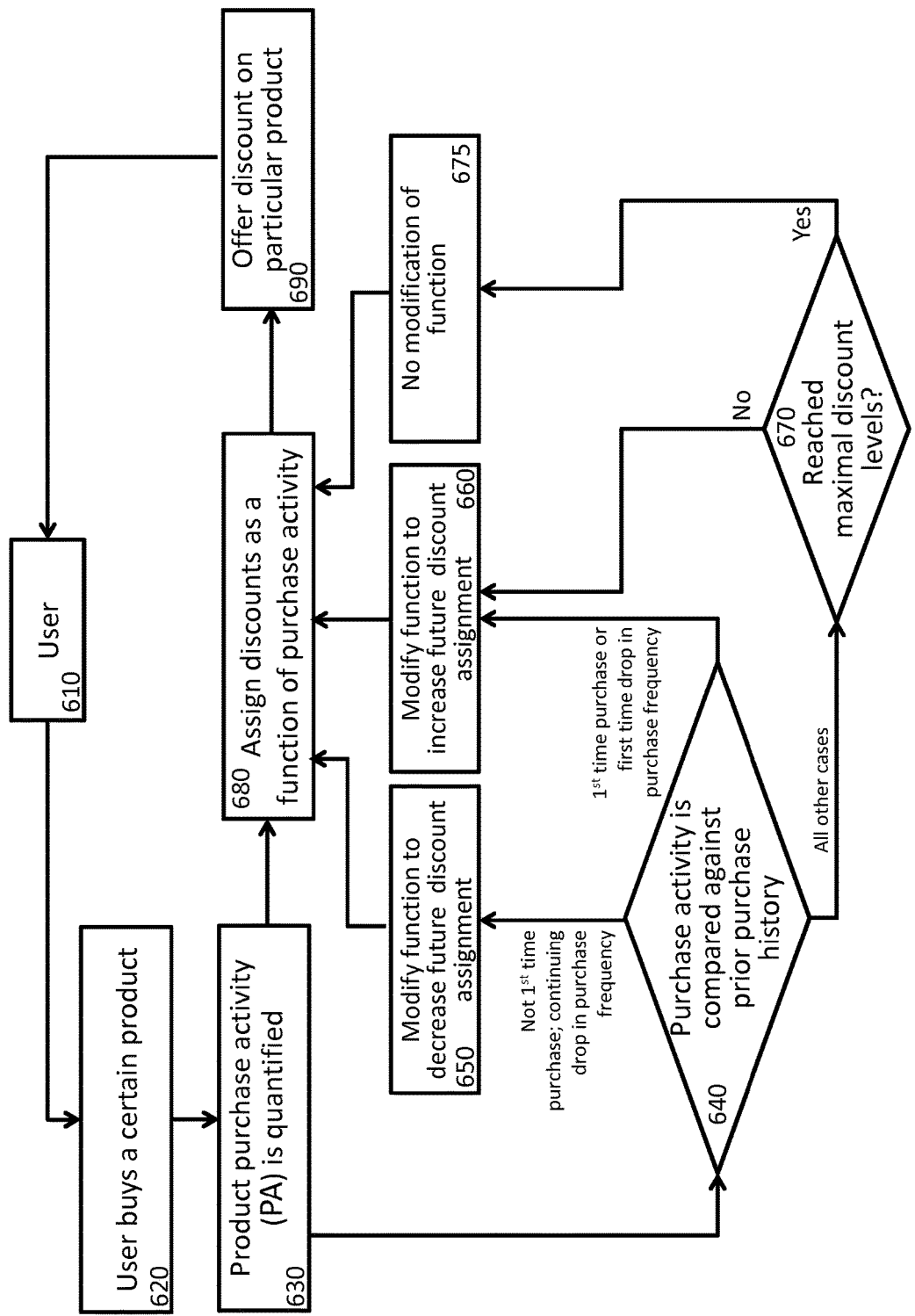
FIG. 6 is a flow chart illustrating another embodiment of a dynamic feed-back loop for providing certain benefits to user by a benefits module of the present invention.

FIG. 6 provides yet another example of one embodiment of a process 600 in which BSA system 100 utilizes its Benefits Engine 132 to motivate and encourage users to use the system and achieve better and more affordable healthcare outcomes.

In one embodiment, module 620 (as an example aspect of modules further described in 780 in FIG. 7) receives and stores quantified record of purchases of a specific product during a given time period directly from the user via Event Monitor 248 of FIG. 2 (348 in FIGS. 3 and 748 in FIG. 7) while in another embodiment module 620 may retrieve this data from User Profile 122 in FIG. 1, and subsequently makes this data available to module 630.

In one embodiment, in module 630, the number of purchases of a specific product (or service) during a period of three months, say, may be recorded as a quantified user related data variable, say $x_{19}$ (as an example aspect of module(s) further described in 784 of FIG. 7). Module 680 utilizes a function (as an example of what is described below in Benefit Function 785 of FIG. 7) that uses $x_{19}$ (in some embodiments in combination with other user related data or other users' data) to calculate discounts to be awarded to user for that specific product (such discounts may be one of the benefits as described in the Benefits module 790). These discounts motivate the user to continue purchasing and using the product and possibly increase the frequency of purchase and usage. In one embodiment module 640 (as an example aspect of module(s) further described in Compliance Behavior Monitor 775 in FIGS. 7 and 875 in FIG. 8) may receive and maintain historical record of $x_{19}$ values and compare such values to facilitate decision making by the system (specifically process 600 or the Benefits Engine 132 in FIG. 1, 732 in FIG. 7) regarding discount levels to be offered to user. If for instance, the product in question was not a first time purchase or there has been a repeated drop in purchase frequency then module 650 may be called upon to modify discount assignment function 680 so as to decrease future discount assignment provided to the user as a way of discouraging drop in use of the product. Similarly, if module 640 determines that this is a first time purchase of the product by the user or that this is the first time that there has been a drop in the user's purchase frequency for this product, then module 660 may be called upon to modify discount assignment function 680 so as to increase future discount assignment provided to the user as a way of encouraging use of said product. In the event, module 640 determines that users purchase activity does not fall under either of the two scenarios described above, then module 670 may be called to help make further decisions regarding discount levels. If the user has reached maximal discount levels that can be offered for this product by BSA system 100 then module 675 may be called, which makes no modification to discount assignment function 680. If however, module 670 determines that maximal discount level has not been reached then module 660 may be called to modify discount assignment function 680 to increase discounts as described earlier.

As is apparent from the above description of FIG. 6, process 600 is an ongoing process designed to "intervene" (by providing and modifying specific product discounts to users) whenever Benefits Engine 132 deems that necessary. Though involved in this process by providing information (e.g., via specific product purchases), users need not initiate the process, and in many cases will be gently nudged by the BSA system 100 towards modifying their behavior towards achieving desired system-wide as well as user specific goals and outcomes. It is also apparent, that different users may have different number of products discounted to different levels.

As described above, one component of Analytics 130 of FIG. 1 is Benefits Engine 732 (132 in FIG. 1), illustrated in block diagram 700 of FIG. 7. As noted above, all user related data, i.e. direct and indirect interactions of the user with the BSA System 100 (which includes all user data from external sources) are stored in User Profile 122 in FIG. 1 of Data Store 720 (120 in FIG. 1). In one embodiment Event Monitor 748 (348 in FIGS. 3 and 248 in FIG. 2) receives all such user related data (URD) and, in addition to sending them to Data Store 720, sends them to Quantified Events 780 of Benefits Engine 732. In another embodiment Quantified Events 780 periodically retrieves URD stored in User Profile of Data Store 720. In yet other embodiments Quantified Events 780 receives information from both Event Monitor 748 and Data Store 720.

In one embodiment illustrated in FIG. 7, Event Quantifier 782 of Quantified Events module 780 first interprets all the URD, and divides it into various different categories, where such categories may include various types of credit related information (e.g. income level, past payment and credit history with the BSA system, FICO score etc., each considered a category), various types of general interactions (e.g. number of queries or check-ins in a given time period as for instance described in FIG. 5, total time spent interacting with the system, total amount of purchases, number of interactions with a specific social network, number of games played, types of geographic locations where user spends time as discerned from client devices etc., each considered a category) as well as dynamically generated additional categories (e.g. the number of purchases of a particular nutritional supplement in a given time period, number of visits to a specific provider etc.). Event Quantifier 782 assigns quantified variables $x_1, x_2, x_3, \ldots$ to represent each of these categories or a combination of these categories. Such variables may or may not be numerical variables (e.g. they could be Boolean variables or a list of possible character strings, such as names of diseases). In one embodiment, the number of check-ins by a user during a week, an integer, could be assigned to $x_1$, for instance. The number of variables being assigned and tracked by Event Quantifier 780 is dynamically created for each user and can vary among users and also for the same user at different times. In one embodiment Quantified Events database 784 may store this multidimensional array $X=(x_1, x_2, x_3, \ldots)$ for individual users and in other embodiments the array X in 784 may be stored in transient memory or in Data Store 720.

Benefits module 790 contains for each user a collection of benefits $Y=y_1, y_2, \ldots$ ). These variables $y_1, y_2, \ldots$ etc., each stand for a specific benefit, and may for instance be points redeemable towards discounts on purchases using the user accounts, interest rates, credit limits, and may include user specific benefits such as discounts on a particular product or service etc., as for instance described in FIG. 6, dynamically generated by Benefits module 790. In one embodiment Benefits database 794 may store this multidimensional array $Y=(y_1, y_2, y_3, \ldots)$ for individual users and in other embodiments the array Y in 794 may be stored in transient memory or in Data Store 720 and Benefits module 790 may retrieve such data from Data Store 720 as needed. In one embodiment Benefits Reporter 792 retrieves information from the Benefits database 794 or its equivalent and provides the information to the user via Event Monitor 748. Benefits Reporter 792 may adjust the timing and format in which benefits are reported to users (e.g. hold reporting of benefits till certain number of them are collected up or till some special day on the user's calendar, or change a discount figure to a more user friendly form, such as that an item now costs half of what user paid for it before, etc.).

Benefits Functions 785 is a collection of functions $F=(f_1, f_2, \ldots$ etc.), one for each benefit $y_1, y_2, \ldots$ etc. in the Benefits module 790. Benefit Function $f_1$ takes the multidimensional array X from Quantified Events module 780 above for a given user and uses a specified formula to calculate a benefit $y_1$. Benefit Function $f_2$ takes the multidimensional array X from Quantified Events module 780 above for same user and uses a possibly different formula to calculate a benefit $y_2$, etc. The functions $f_1, f_2, \ldots$ etc., i.e. the formulas that characterize the functions, are subject to change as needed as for instance described in FIG. 8. An example of simple linear $f_1$ and $f_2$ could be as follows: $f_1(X)=x_1w_{11}+x_2w_{12}+x_3w_{13}+ \ldots$; $f_2(X)=x_1w_{21}+x_2w_{22}+x_3w_{23}+ \ldots$; where $w_{ij}$ (with i varying for each $f_i$, in this case between 1 and 2, and j varying between 1 and n if X has n components) are the weights assigned to the j-th component of X for purposes of calculating the i-th function $f_i$, and any of $w_{ij}$'s may be zero. In various embodiments, other non-linear functions may be employed in an effort to best reflect a particular desired goal (e.g., providing increased credit limits to encourage increased user purchases).

An additional element of the Benefits Engine 732 is the Compliance Behavior Monitor 775 that can dynamically modify the Benefits Functions 785 to achieve certain desired user behavior outcomes as mentioned above. Initially the Benefits Functions 785 may be set in some predetermined form by the BSA System 100 but may be allowed to vary or evolve over time under the influence of Compliance Behavior Monitor 775. The Compliance Behavior Monitor 775 is described further in FIG. 8.

Compliance Behavior Monitor 875 (775 in FIG. 7) compares changes in X, i.e. URD, which in turn relates to changes in user behavior and makes the determination whether certain functions $f_1, f_2, \ldots$ etc. of Benefits Functions 885 (785 in FIG. 7) should be modified so as to increase the credit limit or lower the interest rate or provide specific product discounts in order to encourage the user to increase or maintain the use of the BSA system with a view towards better outcomes for the user and the BSA system as may be desired by the system implementer. In one embodiment, Compliance Behavior Monitor 875 maintains, as shown in 876, an array HX of historical X values for each user starting from $X^{old}$ being the oldest through $X^{old+k}$ being the newest, where k is a positive integer that is implementation dependent. In some embodiments, this array may be initialized to zero values at the beginning. New X values are retrieved as described in 877, from Quantified Events 880 (780 in FIG. 7) and stored, as described in 878, in the next available open position (i.e. all values are still in their initialized state, say zero) in the array. If there are no open positions, then data in $X^{old+1}$ is used to overwrite data in $X^{old}$ and similarly all other entries in the HX array are shifted by 1 position such that the latest X can be written in $X^{old+k}$. Next module 879 compares the trend among the historical X data, i.e. $X^{old+k}, X^{old+k-1}, X^{old+k-2} \ldots$ etc. For instance, if a user's frequency of purchasing a certain product has decreased (as described in FIG. 6) then this trend may be passed on to subsequent modules to initiate appropriate changes in the Benefits Functions 885. In some embodiments, Compliance Behavior Monitor 875 includes a Learning Engine 881 which receives the trends in X form module 879 and designs Benefits Functions modifications 882, which are then implemented in Benefits Functions 885. In some embodiments, the Learning Engine 881 continues to review changes in X, changes in the trends of X etc. in response to its Benefits Functions modifications and continues to adapt its methods or algorithms for designing such modifications. (For example, in FIG. 6 the decision trees 640, 670 and related function modifications 650, 660, 675 may be part of a simple Learning Engine 881, where different types of function modifications are chosen in response to changing purchase date to arrive at optimal user response.) In some embodiments, Learning Engine 881 may be implemented as part of Expert System 134.

It should be noted that the functionality of Benefits Engine 732 may be allocated, in other embodiments, in virtually any manner among Event Monitor 748, Compliance Behavior Monitor 775, Quantified Events 780, Benefits Functions 785, Benefits 790, and other modules on BSA Server 115 and Client Devices 110 without departing from the spirit of this invention. Moreover, various different metrics and functions can be applied to this data in order to implement a feedback loop that assesses user credit, discounts and other benefits, provides such benefits to users, and continually monitors user behavioral interactions to determine the extent to which such metrics and functions should be modified to achieve desired system-wide and personalized user goals.

Finally, Benefits Engine 732 applies, in one embodiment, "user-wide" and "system-wide" constraints which result in modifications to certain Benefits Functions 785 based on constraints beyond monitored changes in relevant X values. For example, a limit to the amount of credit offered any user (or particular users) may be desired. Moreover, such a constraint may be applied on a system-wide basis, resulting in a limit to the aggregate credit offered all users. Similar constraints on discounts and other benefits are also applied in this embodiment.

In one embodiment, benefits "updates" are provided by the Benefits Reporter 792 to Event Monitor 748 on a continual basis, while in other embodiments they are provided on a less frequent periodic or ad hoc basis. As noted above, users then modify their behavior based upon these various incentives, which in turn results in additional (or decreased) incentives as Compliance Behavior Monitor 775 monitors each user's compliance—and this feedback loop continues indefinitely in an effort to encourage increased user participation with BSA system 100, and thus increased user wellness, while reducing user healthcare costs.

The present invention has been described herein with reference to specific embodiments as illustrated in the accompanying drawings. Many variations of the embodiments of the functional components and dynamic operation (including use-case scenarios) of BSA system 100 described above will be apparent to those skilled in the art without departing from the spirit of the present invention, including but not limited to different allocations of the hardware and software functionality of BSA Server 115 and Client Devices 110 among one or more server, desktop, mobile or other computing devices, operating systems and firmware and software modules (including mobile smartphone apps and various networked online devices). Hardware and software functionality can be implemented interchangeably, and computer hardware can include peripherals such as monitors, keyboards, mice, trackpads and a variety of other peripheral I/O, user-wearable and other monitoring devices, including tangible memory and other storage devices (specifically non-transitory computer-accessible storage media in which data and software can be embodied). Moreover, the healthcare sector may be interpreted broadly (encompassing, for example, medicine, nutrition, nutraceuticals, cosmetics, fitness and lifestyle among others), and the functionality described herein may be applied outside of the healthcare sector without departing from the spirit of the present invention.

What is claimed:

1. A benefit-generation system, comprising:
   (a) an event monitor, embodied in non-transitory computer-accessible storage media, that continually monitors and collects event data over time; and
   (b) a benefits engine, embodied in non-transitory computer-accessible storage media, including:
      (i) an event quantifier, that quantifies the event data, generates a first array of quantified events and stores the first array of quantified events in a quantified events database, wherein each element of the first array of quantified events is a variable metric value, wherein each variable metric value has one or more dimensions;
      (ii) a benefits module, that retrieves the first array of quantified events from the quantified events database, retrieves one or more benefit functions from a collection of benefit functions, including a predetermined function, and employs the one or more benefit functions to calculate a second array of benefits from the first array of quantified events, wherein each element of the second array of benefits is calculated based on one or more weighted elements of the first array of quantified events, and wherein the one or more benefit functions determine the weights assigned to each element and the number of elements in the second array of benefits; and
      (iii) a compliance behavior monitor, that detects one or more trends among historical values of the elements of the first array of quantified events over time, by comparing changes in the historical values against a threshold, and, in response to detecting one or more trends, dynamically modifies one or more of the benefit functions contained within the collection of benefit functions used by the benefits module in order to reflect a desired goal, wherein the benefits module utilizes the modified one or more benefit functions on a continuous basis to calculate a new second array of benefits.

2. The benefit-generation system of claim 1, wherein an element of the second array of benefits represents a product discount offered to users of the benefit-generation system for purchases of health-related goods and services.

3. The benefit-generation system of claim 2, wherein one of the one or more benefit functions is dynamically modified for the purpose of increasing or decreasing the product discount.

4. The benefit-generation system of claim 1, wherein an element of the second array of benefits represents credit offered to users of the benefit-generation system for purchases of health-related goods and services, the credit including an interest rate and a credit limit.

5. The benefit-generation system of claim 4, wherein one of the one or more benefit functions is dynamically modified for the purpose of increasing or decreasing the credit limit.

6. The benefit-generation system of claim 4, wherein one of the one or more benefit functions is dynamically modified for the purpose of increasing or decreasing the interest rate.

7. A method for generating benefits, the method comprising the following steps:
   (a) continually monitoring and collecting event data over time;
   (b) quantifying the event data to generate a first array of quantified events and storing the first array of quantified events in a quantified events database, wherein each element of the first array of quantified events is a variable metric value, wherein each variable metric value has one or more dimensions;
   (c) retrieving the first array of quantified events from the quantified events database;
   (d) retrieving one or more benefit functions from a collection of benefit functions, including a predetermined function;
   (e) employing the one or more benefit functions to calculate a second array of benefits from the first array of quantified events, wherein each element of the second array of benefits is calculated based on one or more weighted elements of the first array of quantified events, and wherein the one or more benefit functions determine the weights assigned to each element and the number of elements in the second array of benefits;

(f) detecting one or more trends among historical values of the elements of the first array of quantified events over time, by comparing changes in the historical values against a threshold and, in response to detecting one or more trends, dynamically modifying one or more of the benefit functions contained within the collection of benefit functions in order to reflect a desired goal; and (g) repeating step (d) and step (e) on a continuous basis to calculate a new second array of benefits.

8. The method of claim 7, wherein an element of the second array of benefits represents a product discount offered to users of the benefit-generation system for purchases of health-related goods and services.

9. The method of claim 8, wherein one of the one or more benefit functions is dynamically modified for the purpose of increasing or decreasing the product discount.

10. The method of claim 7, wherein an element of the second array of benefits represents credit offered to users of the benefit-generation system for purchases of health-related goods and services, the credit including an interest rate and a credit limit.

11. The method of claim 10, wherein one of the one or more benefit functions is dynamically modified for the purpose of increasing or decreasing the credit limit.

12. The method of claim 10, wherein one of the one or more benefit functions is dynamically modified for the purpose of increasing or decreasing the interest rate.

\* \* \* \* \*